（12) United States Patent
Williams

(10) Patent No.: US 12,007,384 B1
(45) Date of Patent: Jun. 11, 2024

(54) PORTABLE HOME URINALYSIS MACHINE

(71) Applicant: Ronald Williams, Bronx, NY (US)

(72) Inventor: Ronald Williams, Bronx, NY (US)

( * ) Notice: Subject to any disclaimer, the term of this patent is extended or adjusted under 35 U.S.C. 154(b) by 341 days.

(21) Appl. No.: 17/547,742

(22) Filed: Dec. 10, 2021

(51) Int. Cl.
*G01N 33/493* (2006.01)
*A61B 5/00* (2006.01)
*A61B 5/20* (2006.01)

(52) U.S. Cl.
CPC ......... *G01N 33/493* (2013.01); *A61B 5/0004* (2013.01); *A61B 5/207* (2013.01); *A61B 5/7435* (2013.01)

(58) Field of Classification Search
CPC ........ G01N 33/493; A61B 5/20; A61B 5/207; A61B 5/208; A61B 10/007; A61G 9/00; A61G 9/003; A61G 9/02; A61G 9/006; A47K 11/06; A47K 11/12; E03D 13/005
See application file for complete search history.

(56) References Cited

U.S. PATENT DOCUMENTS

| 4,982,741 | A | 1/1991 | Saito | |
| 5,285,532 | A | 2/1994 | Sealy | |
| 2022/0378348 | A1* | 12/2022 | Oh | A61B 5/208 |
| 2023/0018531 | A1* | 1/2023 | Ogden | A61B 5/208 |

FOREIGN PATENT DOCUMENTS

| KR | 101733175 B1 * | 5/2017 | |
| WO | WO-2009094761 A1 * | 8/2009 | A61B 10/007 |

* cited by examiner

*Primary Examiner* — Herbert K Roberts
(74) *Attorney, Agent, or Firm* — Sanchelima & Associates, P.A.; Christian Sanchelima; Jesus Sanchelima

(57) ABSTRACT

A portable home urinalysis machine including a housing assembly, a chamber assembly, and an electrical assembly. The housing assembly includes a hose connected to a top portion, a chamber portion and a base portion. The container assembly includes two containers mounted on the outside of the chamber. The electrical assembly is enclosed by said base portion. Electrical assembly includes a sensor, a microprocessor, and a display. The electrical assembly configures a system for testing urine. The results of the test are communicated using the display and the results are also sent to an electronic portable device wirelessly.

9 Claims, 3 Drawing Sheets

PORTABLE HOME URINALYSIS MACHINE

BACKGROUND OF THE INVENTION

1. Field of the Invention

The present invention relates to a portable home urinalysis machine and, more particularly, to a portable home urinalysis machine that is easy to use and can show the results of the urinalysis in a display and remotely in an electronic portable device.

2. Description of the Related Art

Several designs for a portable home urinalysis machine have been designed in the past. None of them, however, include a chamber for disposing the urine with a urinalysis system that can send the results wirelessly to an electronic portable device.

Applicant believes that a related reference corresponds to U.S. Pat. No. 5,285,532 issued for a portable urinal device with a fluid collection and disposal box. Applicant believes that another related reference corresponds to U.S. Pat. No. 4,982,741 issued for a urinal or toilet with a built-in urinalysis machine. None of these references, however, teach of a portable home urinalysis machine having a wireless information transmitting system wherein the machine comprises an elevated urinal with a hose leading into a collection chamber for disposing of the urine and an analyzing device located in the bottom of the container and a wireless data transmission device for sending the analysis results to a remote location.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a portable home urinalysis machine that will be able to test the urine of a user, analyze it and communicate results wirelessly.

It is another object of this invention to provide a portable home urinalysis machine that is convenient for using inside a room.

It is still another object of the present invention to provide a portable home urinalysis machine that is ideal for detecting infections or kidney problems.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
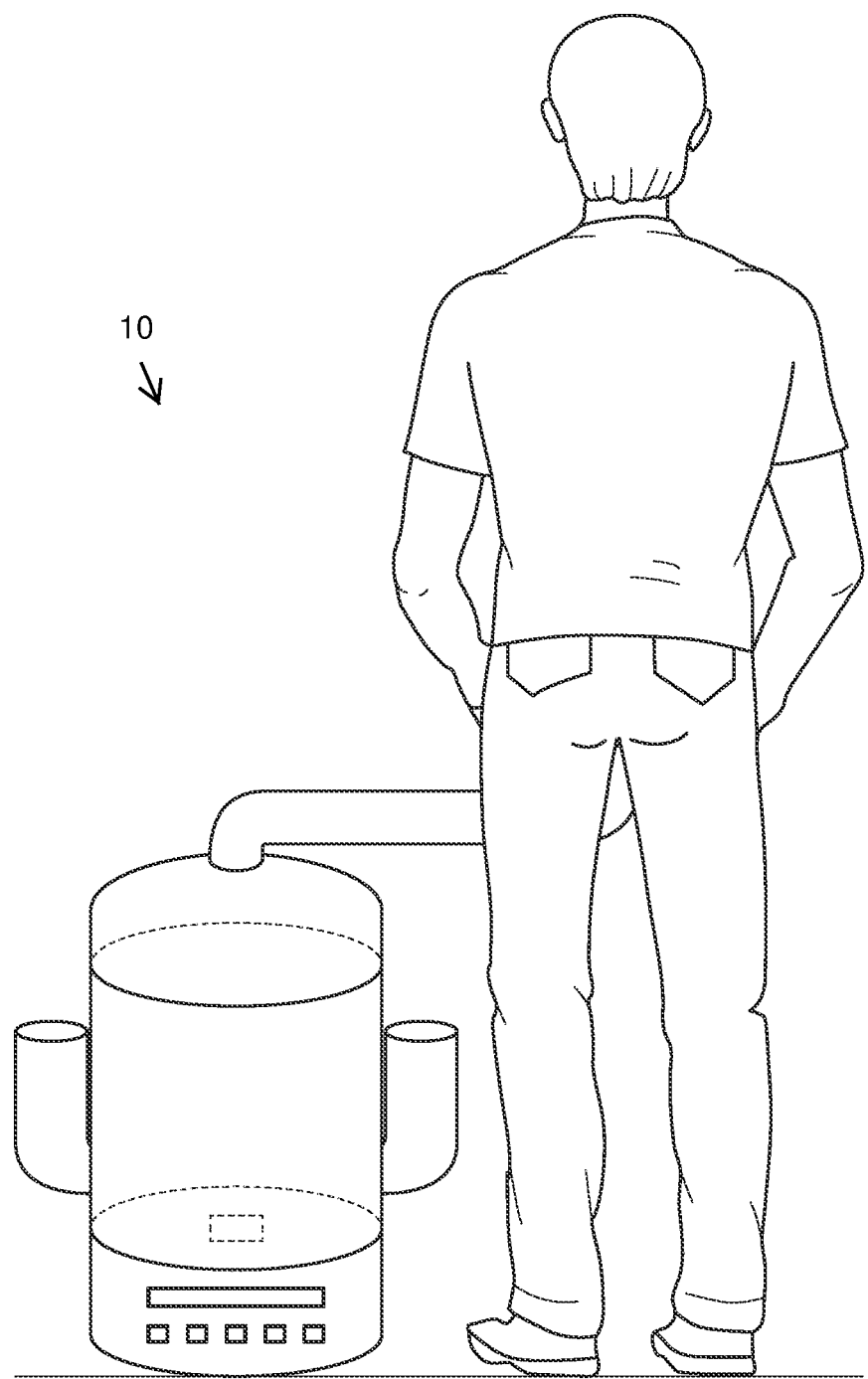
FIG. 1 represents an operational view of the portable home urinalysis machine used by a user to introduce urine for a urine test to be performed.

Referring now to the drawings, where the present invention is generally referred to with numeral 10, it can be observed that it basically includes a housing assembly 20, a container assembly 40, and an electrical assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The housing assembly 20, includes a base portion 22, a central portion 24, and a top portion 26. Base portion 22 is volumetric. In a suitable embodiment the base portion may have a cylindrical shape, nonetheless in other embodiments the base portion 22 may have a cuboid shape, an oval prism shape, a quadrangular prism shape, an irregular shape, or any variation of a volumetric shape. Base portion 22 may be made of a sturdy, durable material. Base portion 22 may be made of acrylic, polycarbonate, polyethylene, polypropylene, polyethylene terephthalate, polyvinyl chloride, acrylonitrile-butadiene-styrene, wood, metal, or any variation thereof. Base portion 22 further includes a top surface 22a and a front surface 22b. Central portion 24 may be mounted on top of the base portion 24. Central portion 24 may be volumetric. Central portion 24 may have a shape that conforms the shape of the base portion 22. However, in other embodiments said central portion 24 may have a cylindrical shape, a cuboid shape, a pyramid shape, a truncated cone shape, a spheric shape, or any variation of a volumetric shape. Central portion 24 may be hollow. Central portion 24 may be a receptacle. Central portion 24 is configured to receive and store urine therein. Central portion 24 may be made of a durable, sturdy, heat resistant material. Central portion 24 may be made of acrylic, polycarbonate, polyethylene, polypropylene, polyethylene terephthalate, polyvinyl chloride, acrylonitrile-butadiene-styrene, wood, metal, or any variation thereof. Top portion 26 is mounted on top of the central portion 24. Top portion 26 is a lid that covers the central portion 24. Top portion 26 may be volumetric. In a suitable embodiment the top portion 26 may have convex shape with a cross section that conforms the shape of the central portion 24. Nonetheless, in other embodiments said top portion 26 may have a rectangular shape, an oval shape, an irregular shape or the like. A hose 28 is connected to the top portion 26. Said hose 28 further includes a first distal end 28a and a second distal end 28b. Hose 28 may have an elongated cylindrical shape, however, in other embodiments said hose 28 may have different elongated shapes. Hose 28 may be made of vinyl, rubber, polyurethane, or the like.

Hose 28 is hollow. The first distal 28a connects the hose 28 to the top portion 26. The second distal end 28b may have a hollow truncated cone shape defining a funnel. The hose 28 permits the pass of substances therethrough. In conjunction the hose 28 connected to the top portion 26 allows exterior substances to be introduced into the central portion 24. In a suitable embodiment the central portion 24 is configured to receive urine therein. Urine may be introduced through said hose 28.

Figure 2:
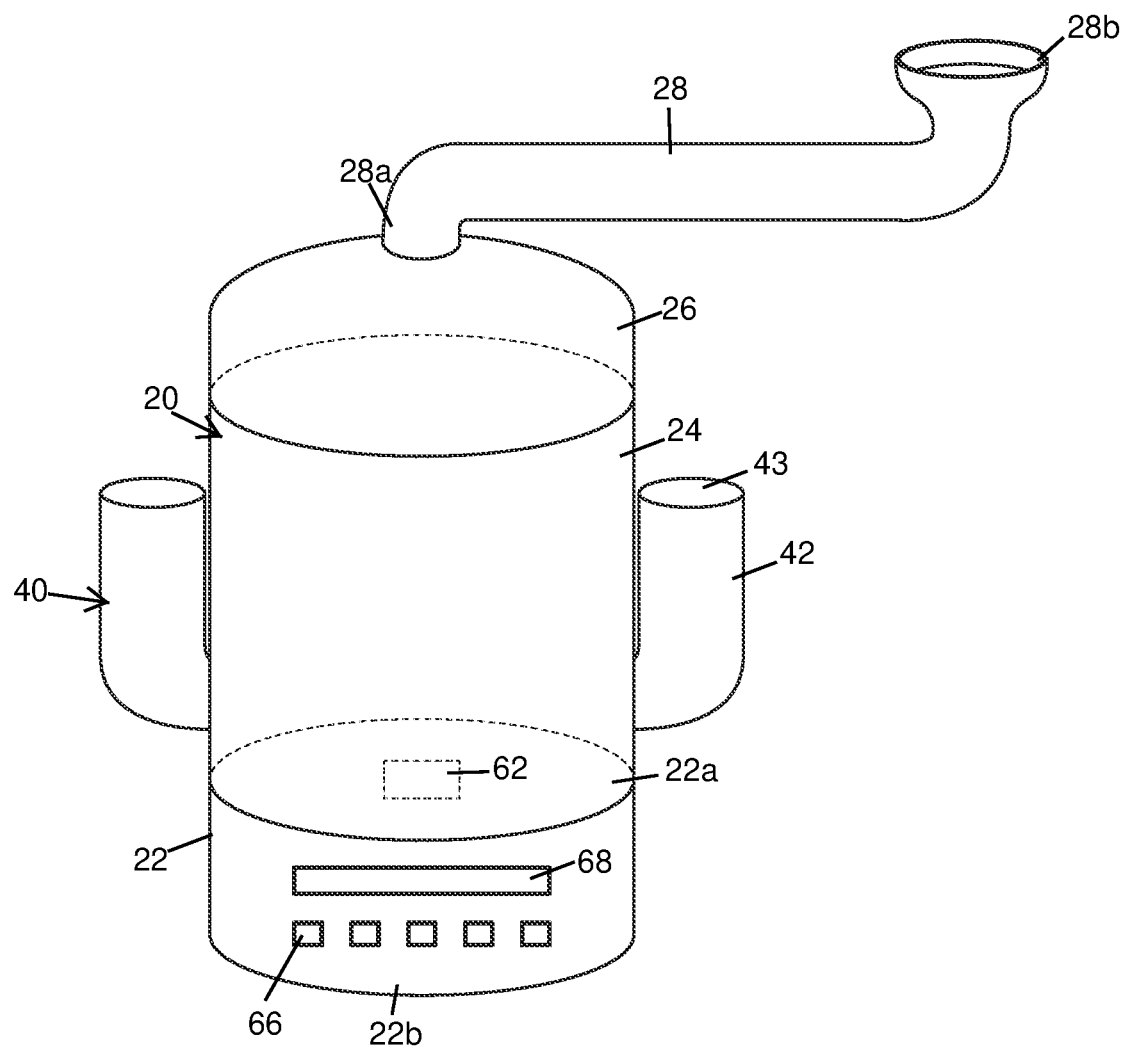
FIG. 2 shows an isometric view of the housing assembly 20 having the base portion 22, the central portion 24, the top portion 25. The display 68, the plurality of buttons 66. Please draw image 2 isometrically.
Figure 3:
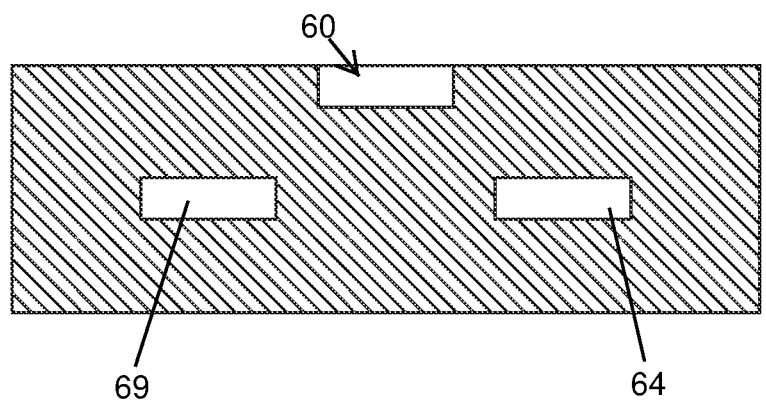
FIG. 3 illustrates a cross sectional view of the base portion 22 showing the microcontroller 64, the transmitter unit 69, and the sensor 62.
Figure 4:
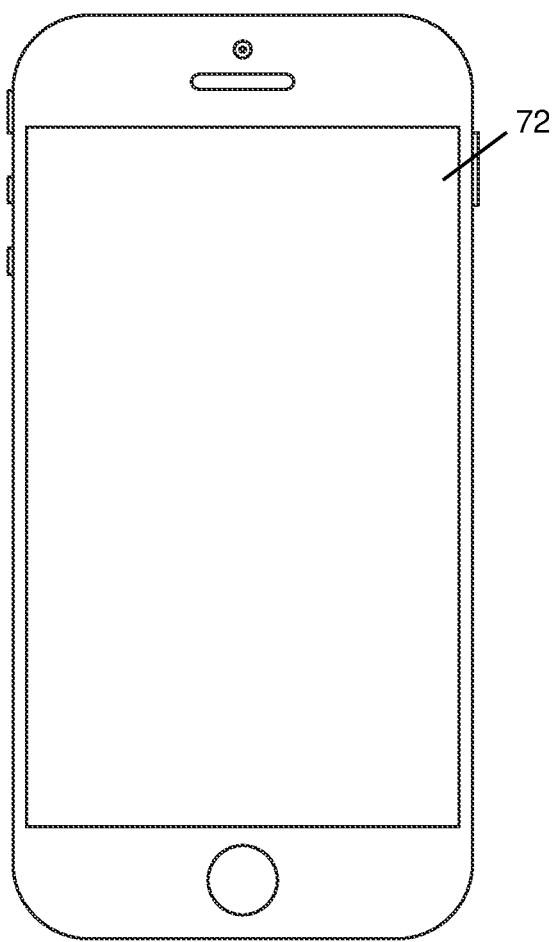
FIG. 4 is a representation of the portable electronic device 72 that receives the results of the urinalysis performed by the microcontroller 64.

The container assembly 40 includes a plurality of containers 42. Each container from the plurality of containers 42 may be made of acrylic, polycarbonate, polyethylene, polypropylene, polyethylene terephthalate, polyvinyl chloride, acrylonitrile-butadiene-styrene, wood, metal, or any variation thereof. Each container may have an elongated volumetric shape. In a suitable embodiment each container may have an elongated cylindrical shape. However, in other embodiments each container from said plurality of containers 42 may have a cuboid shape, a pyramid shape, a conical shape, a prism shape, or the like. Each container may be opened at a top end 43. Each container may be placed vertically in abutting contact with the central portion 24 as shown in FIG. 2. Nevertheless, the plurality of containers 42 may be located wheresoever on the central portion 24. In a suitable embodiment one container from the plurality of containers 42 is configured to receive garbage therein, whereas another container from said plurality of containers 42 is be configured to hold wet wipes.

The electrical assembly 60 includes a sensor 62, a microcontroller 64, a plurality of buttons 66, a display 68, and a transmitter unit 69. Depending on the type of sensor used for a urinalysis analysis the sensor 62 may be placed in such a way that sensor 62 may have in direct contact with an interior of the central portion 24. Sensor 62 is configured to be used as an auxiliar tool for performing a urinalysis. Urinalysis may be performed by inspection, with this method urine is visually analyzed in order to find abnormalities in a color of the urine, smell of urine, or turbidity of urine. Urinalysis may also be performed using test strips. In one embodiment sensor 62 may be a color sensor which is a type of photoelectric sensor capable of detecting the color of an object. In another embodiment sensor 62 may be an odor sensor for detecting predetermined odors associated to preconfigured indications such as the presence of bacteria. In another embodiment the sensor 62 may be an electronic turbidity meter for measuring turbidity in urine. In yet another embodiment said sensor 62 may be a test strip to measure concentration of chemicals or characteristics of urine. Test strips convey results visually showing different colors. Colors shown by test strip then may be detected using color sensors. Sensor 62 provides an output signal that is acquired by the microcontroller 64. Microcontroller 64 receives the output signal from the sensor 62. Microcontroller 64 may process the output signal giving predetermined results associated with predetermined output signals. Microcontroller 64 is configured to perform a urinalysis using the output signal from the sensor 62. Results given by the urinalysis performed by the microcontroller 64 are sent wirelessly to a portable electronic device 72. Results given by the urinalysis performed by the microcontroller 64 are shown on the display 68. Microcontroller 64 may be enclosed by the base portion 22. Transmitter unit 69 is connected to said microcontroller 64, connection may be done using electrical wires. Transmitter unit 69 may transmit a signal having format of an electromagnetic radiation, such signal may be audio, supersonic, ultrasonic, infrared, RF, Wi-Fi, Bluetooth™, or any variation thereof. Transmitter unit 69 transmits a signal that contains the results of the urinalysis wirelessly. In a suitable embodiment the transmitter unit 69 may send said signal to the portable electronic device 72, however, in other embodiments devices such as tablets, laptops, PCs, or the like may be able to receive the signal sent by the transmitter unit 69. Display 68 may be located on said front surface 22b. In a suitable embodiment display 68 may be an organic light-emitting diode (OLED) display, nonetheless, other variety of displays may be used such as field sequential color LCD display, EBT LCD display, thin-film-transistor LCD display, or any variation thereof. The display 68 may be used to present information in visual form. Results given by the microcontroller 64 may be shown in the display 68. Plurality of buttons 66 may be placed proximal to the display 68. Plurality of buttons may be located on the front surface 22b. Plurality of buttons permit to configure settings for performing the urinalysis and how information may be displayed.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A portable home urinalysis machine, comprising:
   a) a housing assembly having a base portion, a central portion mounted on top of the base portion, and a top portion mounted on top of the central portion, a hose is connected to said top portion, the hose is for conducting substances into the central portion;
   b) a container assembly including a plurality of containers mounted in abutting contact with an outside of the central portion, said plurality of containers spaced apart circumferentially about the outside of the central portion, wherein each container from said plurality of containers is opened at a top end, one container is for disposing garbage, and another container is configured to hold wet wipes; and
   c) an electrical assembly including a sensor, a microcontroller, a display, and a plurality of buttons, said sensor is enclosed by the base portion, the sensor is in contact with the central portion, the sensor is configured to measure characteristics of a urine comprising color, odor, and turbidity, the sensor is configured to output a signal containing information about the urine, the microcontroller is configured to acquire information sent by the sensor, said microcontroller is configured to process the output signal giving predetermined results associated with predetermined signals, the microcontroller is configured to perform a urinalysis using the output signal from the sensor, said plurality of buttons permit to configure settings for performing the urinalysis and how information may be displayed, and the machine is configured to wirelessly send, to an electronic portable device, results given by the urinalysis performed by the microcontroller.

2. The portable home urinalysis machine of claim 1, wherein said hose is connected to said top portion, a first distal end of said hose is configured to conduct substances to an inside of the central portion, and the central portion is a receptacle capable of receiving urine therein.

3. The portable home urinalysis machine of claim 2, wherein said hose has a second distal end having a hollow truncated cone shape defining a funnel.

4. The portable home urinalysis machine of claim 1, wherein said electrical assembly includes a transmitter unit.

5. The portable home urinalysis machine of claim 4, wherein said transmitter unit wirelessly transmits an electromagnetic radiation signal that contains the results of the urinalysis performed by the microcontroller.

6. The portable home urinalysis machine of claim 4, wherein said display is located on a front surface of the base portion, and the display is configured to show the results given by the microcontroller.

7. The portable home urinalysis machine of claim 4, wherein said plurality of buttons is placed proximal to the display, and the plurality of buttons is located on a front surface of the base portion.

8. A portable home urinalysis machine, comprising:
a) a housing assembly having a base portion, a central portion mounted on top of the base portion, and a top portion mounted on top of the central portion, a hose is connected to said top portion, the hose is for conducting substances into the central portion;
b) a container assembly including a plurality of containers mounted in abutting contact with an outside of the central portion, said plurality of containers spaced apart circumferentially about the outside of the central portion, wherein each container from said plurality of containers is opened at a top end, one container is for disposing garbage, and another container is configured to hold wet wipes; and
c) an electrical assembly including a sensor, a microcontroller, a transmitter unit a display, and a plurality of buttons, said sensor is enclosed by the base portion, the sensor is in contact with the central portion, the sensor is configured to measure characteristics of a urine comprising color, odor, and turbidity, the sensor is configured to output a signal containing information about the urine, the microcontroller is configured to acquire information sent by the sensor, said microcontroller is configured to process the output signal giving predetermined results associated with predetermined signals, the microcontroller is configured to perform a urinalysis using the output signal from the sensor, said display is located on a front surface of the base portion, said plurality of buttons permit to configure settings for performing the urinalysis and how information may be displayed, and the transmitter unit is configured to wirelessly send, to an electronic portable device, an electromagnetic radiation signal comprising results given by the urinalysis performed by the microcontroller.

9. A portable home urinalysis machine, consisting of:
a) a housing assembly having a base portion, a central portion mounted on top of the base portion, and a top portion mounted on top of the central portion, a hose is connected to said top portion, the hose is for conducting substances into the central portion;
b) a container assembly including a plurality of containers mounted in abutting contact with an outside of the central portion, said plurality of containers spaced apart circumferentially about the outside of the central portion, wherein each container from said plurality of containers is opened at a top end, one container is for disposing garbage, and another container is configured to hold wet wipes; and
c) an electrical assembly including a sensor, a microcontroller, a transmitter unit a display, and a plurality of buttons, said sensor is enclosed by the base portion, the sensor is in contact with the central portion, the sensor is configured to measure characteristics of a urine comprising color, odor, and turbidity, the sensor is configured to output a signal containing information about the urine, the microcontroller is configured to acquire information sent by the sensor, said microcontroller is configured to process the output signal giving predetermined results associated with predetermined signals, the microcontroller is configured to perform a urinalysis using the output signal from the sensor, said display is located on a front surface of the base portion, said plurality of buttons permit to configure settings for performing the urinalysis and how information may be displayed, and the transmitter unit is configured to wirelessly send, to an electronic portable device, an electromagnetic radiation signal comprising results given by the urinalysis performed by the microcontroller.

* * * * *